US008747891B2

(12) United States Patent
Kester et al.

(10) Patent No.: US 8,747,891 B2
(45) Date of Patent: Jun. 10, 2014

(54) CERAMIDE ANIONIC LIPOSOME COMPOSITIONS

(75) Inventors: Mark Kester, Harrisburg, PA (US); Sriram S. Shanmugavelandy, Hershey, PA (US); Todd Fox, Hershey, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 13/468,578

(22) Filed: May 10, 2012

(65) Prior Publication Data

US 2012/0288556 A1    Nov. 15, 2012

Related U.S. Application Data

(60) Provisional application No. 61/484,496, filed on May 10, 2011.

(51) Int. Cl.
*A61K 31/475* (2006.01)
*A61K 9/127* (2006.01)
*A61K 31/44* (2006.01)
*A61K 31/7076* (2006.01)
*A61P 35/00* (2006.01)
*B01J 13/04* (2006.01)

(52) U.S. Cl.
USPC ............. 424/450; 514/283; 514/350; 514/46; 264/41

(58) Field of Classification Search
USPC ....................................................... 424/450
See application file for complete search history.

(56) References Cited

U.S. PATENT DOCUMENTS

| | | | |
|---|---|---|---|
| 7,244,450 B2 * | 7/2007 | Sarris et al. | 424/450 |
| 7,311,924 B2 | 12/2007 | Sarris et al. | |
| 2003/0026831 A1 * | 2/2003 | Lakkaraju et al. | 424/450 |
| 2004/0253302 A1 | 12/2004 | Sarris et al. | |
| 2005/0025820 A1 | 2/2005 | Kester et al. | |
| 2005/0267060 A1 | 12/2005 | Robertson et al. | |
| 2006/0083780 A1 | 4/2006 | Heyes et al. | |
| 2006/0198882 A1 | 9/2006 | Barenholz et al. | |
| 2007/0003607 A1 | 1/2007 | Awasthi et al. | |
| 2007/0031480 A1 | 2/2007 | Mayer et al. | |
| 2007/0116753 A1 | 5/2007 | Hong et al. | |
| 2008/0008749 A1 | 1/2008 | Pearlman et al. | |
| 2009/0087479 A1 | 4/2009 | Lau et al. | |
| 2010/0080773 A1 | 4/2010 | Geho et al. | |
| 2010/0247625 A1 | 9/2010 | Geho et al. | |
| 2010/0310599 A1 | 12/2010 | Geho et al. | |
| 2011/0229529 A1 | 9/2011 | Irvine et al. | |
| 2012/0009243 A1 * | 1/2012 | Vikbjerg et al. | 424/450 |

FOREIGN PATENT DOCUMENTS

WO    WO-9930686    6/1999

OTHER PUBLICATIONS

Taneja D, High entrapment liposomes for 6-mercaptopurine-a prodrug approach, Dekker, Drug Dev and Indus Pharm, 2000, 23(1), 1315-1319.*
Kulkarni, S. et al., Factors affecting microencapsulation of drugs in liposomes, *Journal of Microencapsulation*, 12(3): 229-46, May-Jun. 1995 (Abstract only).
Maswadeh, H. et al., Encapsulation of vinblastine into new liposome formulations prepared from triticum (wheat germ) lipids and its activity against human leukemic cell lines, *Anticancer Research*, 20(6B): 4385-90, Nov.-Dec. 2000.
Maswadeh, H. et al., Accumulation of vinblastine into transfersomes and liposomes in response to a transmembrane ammonium sulfate gradient and their cytotoxic/cytostatic activity in vitro, *Anticancer Research*, 21(4A): 2577-83, Jul.-Aug. 2001.
Maswadeh, H. et al., In-vitro cytotoxic/cytostatic activity of anionic liposomes containing vinblastine against leukaemic human cell lines, *The Journal of Pharmacy and Pharmacology*, 54(2): 189-96, Feb. 2002.
Noble, C. et al., Characterization of highly stable liposomal and immunoliposomal formulations of vincristine and vinblastine, *Cancer Chemotherapy and Pharmacology*, 64: 741-51, 2009.
Stover, T. et al., Liposomal Delivery Enhances Short-Chain Ceramide-Induced Apoptosis of Breast Cancer Cells, *The Journal of Pharmacology and Experimental Therapeutics*, 307(2): 468-75, 2003.
Stover, T. et al., Systemic Delivery of Liposomal Short-Chain Ceramide Limits Solid Tumor Growth in Murine Models of Breast Adenocarcinoma, *Clinical Cancer Research*, 11(9): 3465-74, May 1, 2005.
Zhigaltsev et al., Liposome-encapsulated vincristine, vinblastine and vinorelbine: a comparative study of drug loading and retention, *Journal of Controlled Release*, 104(1): 103-11, May 5, 2005 (Abstract only).
Tran, M. et al., Combining nanoliposomal ceramide with sorafenib synergistically inhibits melanoma and breast cancer cell survival to decrease tumor development, *Clinical Cancer Research*, 14(11): 3571-81, Jun. 2008.
Drummond, et al., Optimizing liposomes for delivery of chemotherapeutic agents to solid tumors, *Pharmacological Reviews*, 51(4): 691-743, 1999.
Maurer, N. et al., Developments in liposomal drug delivery systems, *Expert Opinion on Biological Therapy*, 1(6): 1-25, 2001.

\* cited by examiner

*Primary Examiner* — Frederick Krass
*Assistant Examiner* — Celeste A Roney
(74) *Attorney, Agent, or Firm* — McKee, Voorhees & Sease, P.L.C.

(57) ABSTRACT

Described herein are pharmaceutical compositions according to aspects of the present invention which include one or more hydrophilic antineoplastic chemotherapeutics, such as vinca alkyloid antineoplastic chemotherapeutics, encapsulated in ceramide anionic liposomes. Methods of treatment of a subject having cancer using the pharmaceutical compositions are described, along with methods of making ceramide anionic liposomes which encapsulate one or more hydrophilic antineoplastic chemotherapeutics in the aqueous interior of the ceramide anionic liposomes.

13 Claims, 5 Drawing Sheets

CERAMIDE ANIONIC LIPOSOME COMPOSITIONS

REFERENCE TO RELATED APPLICATION

This application claims priority from U.S. Provisional Patent Application Ser. No. 61/484,496, filed May 10, 2011, the entire content of which is incorporated herein by reference.

FIELD OF THE INVENTION

The present invention relates generally to liposome compositions for delivery of antineoplastic chemotherapeutics to treat cancer. Aspects of the present invention relate to ceramide anionic liposome compositions containing hydrophilic antineoplastic chemotherapeutics and/or vinca alkyloids.

BACKGROUND OF THE INVENTION

There is a continuing need for anti-cancer compositions and methods of treatment. Methods of encapsulating hydrophilic antineoplastic therapeutics are required.

SUMMARY OF THE INVENTION

Pharmaceutical compositions are provided according to aspects of the present invention which include a hydrophilic antineoplastic chemotherapeutic encapsulated in ceramide anionic liposomes.

According to aspects of the present invention the hydrophilic antineoplastic chemotherapeutic is a vinca alkyloid antineoplastic chemotherapeutic encapsulated in ceramide anionic liposomes.

According to aspects of the present invention the hydrophilic antineoplastic chemotherapeutic is vinblastine, vincristine, vinglycinate, vinorelbine, vindesine, sorafenib, cladribine and a combination of any two or more thereof encapsulated in ceramide anionic liposomes.

Pharmaceutical compositions are provided according to aspects of the present invention which include one or more hydrophilic antineoplastic chemotherapeutics encapsulated in ceramide anionic liposomes wherein the amount of the drug encapsulated in the liposomes compared to the amount of total lipids in the liposomes is in the range of about 1:1-1:100.

Pharmaceutical compositions are provided according to aspects of the present invention which include one or more hydrophilic antineoplastic chemotherapeutics encapsulated in ceramide anionic liposomes wherein the ceramide anionic liposomes comprise a 3-5.5:1-4:1:3 ratio of neutral lipid:pegylated neutral lipid:anionic lipid:one or more of C4 ceramide, C6 ceramide, C8 ceramide, C10 ceramide, C12 ceramide, C14 ceramide, C16 ceramide and C18 ceramide.

Pharmaceutical compositions are provided according to aspects of the present invention which include one or more hydrophilic antineoplastic chemotherapeutics encapsulated in ceramide anionic liposomes wherein the ceramide anionic liposomes comprise a 3-5.5:1-4:1:3 ratio of neutral lipid:pegylated neutral lipid:anionic lipid:one or more of C4 ceramide, C6 ceramide, C8 ceramide, C10 ceramide, C12 ceramide, C14 ceramide, C16 ceramide and C18 ceramide, and wherein the neutral lipid is a mixture of DSPC and DOPE, wherein the modified neutral lipid is a mixture of PEG(2000)-DSPE and N-Octanoyl-Sphingosine-1-succinyl(methoxy(polyethylene)glycol)750, and wherein the anionic lipid is dihexadecyl phosphate.

Pharmaceutical compositions are provided according to aspects of the present invention which include vinblastine encapsulated in ceramide anionic liposomes wherein the ceramide anionic liposomes comprise a 3-5.5:1-4:1:3 ratio of neutral lipid:pegylated neutral lipid:anionic lipid: one or more of C4 ceramide, C6 ceramide, C8 ceramide, C10 ceramide, C12 ceramide, C14 ceramide, C16 ceramide and C18 ceramide, and wherein the neutral lipid is a mixture of DSPC and DOPE, wherein the modified neutral lipid is a mixture of PEG(2000)-DSPE and N-Octanoyl-Sphingosine-1-succinyl(methoxy(polyethylene)glycol)750, and wherein the anionic lipid is dihexadecyl phosphate.

Pharmaceutical compositions are provided according to aspects of the present invention which include vinblastine, vincristine, vinglycinate, vinorelbine, vindesine, sorafenib, cladribine, or a combination of any two or more thereof, encapsulated in ceramide anionic liposomes wherein the ceramide anionic liposomes comprise a 3-5.5:1-4:1:3 ratio of neutral lipid:pegylated neutral lipid:anionic lipid:one or more of C4 ceramide, C6 ceramide, C8 ceramide, C10 ceramide, C12 ceramide, C14 ceramide, C16 ceramide and C18 ceramide, and wherein the neutral lipid is a mixture of DSPC and DOPE, wherein the modified neutral lipid is a mixture of PEG(2000)-DSPE and N-Octanoyl-Sphingosine-1-succinyl (methoxy(polyethylene)glycol)750, and wherein the anionic lipid is dihexadecyl phosphate.

Pharmaceutical compositions are provided according to aspects of the present invention which include one or more hydrophilic antineoplastic chemotherapeutics encapsulated in ceramide anionic liposomes wherein the liposomes comprise at least one pegylated neutral lipid, wherein the total amount of pegylated neutral lipid is an amount in the range of 5-20 Molar percent, inclusive, and wherein at least half of the amount of included modified neutral lipid is N-Octanoyl-Sphingosine-1-succinyl(methoxy(polyethylene)glycol)750; at least one anionic lipid, wherein the total amount of anionic lipid is an amount in the range of 5-15 Molar percent, inclusive; a ceramide selected from C4 ceramide, C6 ceramide, C8 ceramide, C10 ceramide, C12 ceramide, C14 ceramide, C16 ceramide and C18 ceramide, or a combination of any two or more thereof, in an amount in the range of 1-40 Molar percent, inclusive; and cationic or neutral lipids, with the proviso that the resulting ceramide anionic liposomes have a net negative charge at physiological pH.

Pharmaceutical compositions are provided according to aspects of the present invention which include one or more hydrophilic antineoplastic chemotherapeutics encapsulated in ceramide anionic liposomes wherein the liposomes comprise at least one pegylated neutral lipid, wherein the total amount of pegylated neutral lipid is an amount in the range of 5-20 Molar percent, inclusive, and wherein at least half of the amount of included modified neutral lipid is N-Octanoyl-Sphingosine-1-succinyl(methoxy(polyethylene)glycol)750 (PEG(750) C8); at least one anionic lipid, wherein the total amount of anionic lipid is an amount in the range of 5-15 Molar percent, inclusive; C6 ceramide in an amount in the range of 1-40 Molar percent, inclusive; and cationic or neutral lipids, with the proviso that the resulting ceramide anionic liposomes have a net negative charge at physiological pH.

Pharmaceutical compositions are provided according to aspects of the present invention which include one or more hydrophilic antineoplastic chemotherapeutics encapsulated in ceramide anionic liposomes wherein the liposomes comprise at least one pegylated neutral lipid, wherein the total amount of pegylated neutral lipid is an amount in the range of 5-20 Molar percent, inclusive, and wherein at least half of the amount of included modified neutral lipid is N-Octanoyl- Sphingosine-1-succinyl(methoxy(polyethylene)glycol)750 (PEG(750) C8); at least one anionic lipid, wherein the total amount of anionic lipid is an amount in the range of 5-15 Molar percent, inclusive; C8 ceramide in an amount in the range of 1-40 Molar percent, inclusive; and cationic or neutral lipids, with the proviso that the resulting ceramide anionic liposomes have a net negative charge at physiological pH.

Pharmaceutical compositions are provided according to aspects of the present invention which include one or more hydrophilic antineoplastic chemotherapeutics encapsulated in ceramide anionic liposomes wherein the liposomes comprise at least one pegylated neutral lipid, wherein the total amount of pegylated neutral lipid is an amount in the range of 5-20 Molar percent, inclusive, and wherein at least half of the amount of included modified neutral lipid is N-Octanoyl-Sphingosine-1-succinyl(methoxy(polyethylene)glycol)750 (PEG(750) C8); at least one anionic lipid, wherein the total amount of anionic lipid is an amount in the range of 5-15 Molar percent, inclusive; C6 ceramide and C8 ceramide in an amount in the range of 1-40 Molar percent, inclusive; and cationic or neutral lipids, with the proviso that the resulting ceramide anionic liposomes have a net negative charge at physiological pH.

Methods of treatment of a subject in need thereof are provided according to aspects of the present invention which include administration of a therapeutically effective amount of a pharmaceutical composition according to aspects of the present invention which includes a hydrophilic antineoplastic chemotherapeutic encapsulated in ceramide anionic liposomes.

Methods of treatment of a subject having, or at risk of having, cancer are provided according to aspects of the present invention which include administration of a therapeutically effective amount of a pharmaceutical composition according to aspects of the present invention which includes a hydrophilic antineoplastic chemotherapeutic encapsulated in ceramide anionic liposomes.

Methods of treatment of a subject having, or at risk of having, cancer are provided according to aspects of the present invention which include administration of a therapeutically effective amount of a pharmaceutical composition according to aspects of the present invention which includes a hydrophilic antineoplastic chemotherapeutic encapsulated in ceramide anionic liposomes and further include administration of an adjunct anti-cancer treatment.

Methods of producing a pharmaceutical composition including a hydrophilic antineoplastic chemotherapeutic encapsulated in ceramide anionic liposomes are provided according to aspects of the present invention which include providing a lipid mixture comprising at least one pegylated neutral lipid, wherein the total amount of pegylated neutral lipid is an amount in the range of 5-20 Molar percent, inclusive, and wherein at least half of the amount of included pegylated neutral lipid is N-Octanoyl-Sphingosine-1-succinyl(methoxy(polyethylene)glycol)750; at least one anionic lipid, wherein the total amount of anionic lipid is an amount in the range of 5-15 Molar percent, inclusive; C4 ceramide, C6 ceramide, C8 ceramide, C10 ceramide, C12 ceramide, C14 ceramide, C16 ceramide, C18 ceramide, or a combination of any two or more thereof, in an amount in the range of 1-40 Molar percent, inclusive; and cationic or neutral lipids, with the proviso that the resulting lipid mixture has a net negative charge at physiological pH; sonicating the lipid mixture in the presence of an amount of a antineoplastic chemotherapeutic at a temperature in the range of 55-75 degrees Celsius, inclusive, to produce a sonicated mixture; and passing the sonicated mixture through a filter having pores of a desired size to produce liposomes having the desired size, at a temperature in the range of 67-75 degrees Celsius, producing a population of ceramide anionic liposomes, wherein the population comprises greater than 10%, greater than 25%, greater than 50% or in the range of about 15-75% of the amount of the antineoplastic chemotherapeutic, wherein the amount of the drug encapsulated in the liposomes compared to the amount of total lipids in the liposomes is in the range of about 1:1-1:100.

Methods of producing a pharmaceutical composition including a hydrophilic antineoplastic chemotherapeutic encapsulated in ceramide anionic liposomes are provided according to aspects of the present invention which include providing a lipid mixture comprising at least one pegylated neutral lipid, wherein the total amount of pegylated neutral lipid is an amount in the range of 5-20 Molar percent, inclusive, and wherein at least half of the amount of included pegylated neutral lipid is N-Octanoyl-Sphingosine-1-succinyl(methoxy(polyethylene)glycol)750; at least one anionic lipid, wherein the total amount of anionic lipid is an amount in the range of 5-15 Molar percent, inclusive; C6 ceramide, C8 ceramide, or a combination thereof, in an amount in the range of 1-40 Molar percent, inclusive; and cationic or neutral lipids, with the proviso that the resulting lipid mixture has a net negative charge at physiological pH; sonicating the lipid mixture in the presence of an amount of a antineoplastic chemotherapeutic at a temperature in the range of 55-75 degrees Celsius, inclusive, to produce a sonicated mixture; and passing the sonicated mixture through a filter having pores of a desired size to produce liposomes having the desired size, at a temperature in the range of 67-75 degrees Celsius, producing a population of ceramide anionic liposomes, wherein the population comprises greater than 10%, greater than 25%, greater than 50% or in the range of about 15-75% of the amount of the antineoplastic chemotherapeutic, wherein the amount of the drug encapsulated in the liposomes compared to the amount of total lipids in the liposomes is in the range of about 1:1-1:100.

According to aspects of methods of producing a pharmaceutical composition including a hydrophilic antineoplastic chemotherapeutic encapsulated in ceramide anionic liposomes of the present invention, the antineoplastic chemotherapeutic is a vinca alkyloid antineoplastic chemotherapeutic.

According to aspects of methods of producing a pharmaceutical composition including a hydrophilic antineoplastic chemotherapeutic encapsulated in ceramide anionic liposomes of the present invention, the antineoplastic chemotherapeutic is selected from the group consisting of: vinblastine, vincristine, vinglycinate, vinorelbine, vindesine, sorafenib, cladribine and a combination of any two or more thereof.

DETAILED DESCRIPTION OF THE INVENTION

Figure 1:
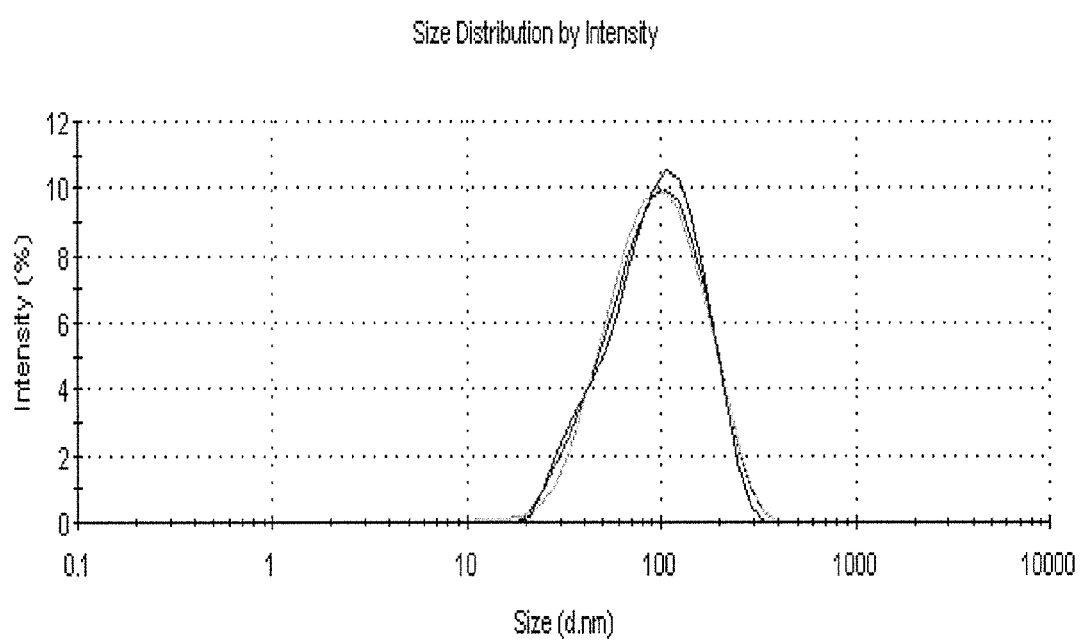
FIG. 1 is a graph showing results of dynamic light scattering analysis indicating stability of ceramide anionic liposome compositions of the present invention.

Scientific and technical terms used herein are intended to have the meanings commonly understood by those of ordinary skill in the art. Such terms are found defined and used in context in various standard references illustratively including J. Sambrook and D. W. Russell, Molecular Cloning: A Laboratory Manual, Cold Spring Harbor Laboratory Press; 3rd Ed., 2001; F. M. Ausubel, Ed., Short Protocols in Molecular Biology, Current Protocols; 5th Ed., 2002; B. Alberts et al., Molecular Biology of the Cell, 4th Ed., Garland, 2002; D. L. Nelson and M. M. Cox, Lehninger Principles of Biochemistry, 4th Ed., W.H. Freeman & Company, 2004; Engelke, D. R., RNA Interference (RNAi): Nuts and Bolts of RNAi Technology, DNA Press LLC, Eagleville, Pa., 2003; Herdewijn, P. (Ed.), Oligonucleotide Synthesis: Methods and Applications, Methods in Molecular Biology, Humana Press, 2004; A. Nagy, M. Gertsenstein, K. Vintersten, R. Behringer, Manipulating the Mouse Embryo: A Laboratory Manual, 3rd edition, Cold Spring Harbor Laboratory Press; Dec. 15, 2002, ISBN-10: 0879695919; Kursad Turksen (Ed.), Embryonic stem cells: methods and protocols in Methods Mol Biol. 2002; 185, Humana Press; Current Protocols in Stem Cell Biology, ISBN: 9780470151808.

The singular terms "a," "an," and "the" are not intended to be limiting and include plural referents unless explicitly state or the context clearly indicates otherwise.

Ceramide anionic liposome compositions containing at least one hydrophilic antineoplastic chemotherapeutic and methods for use thereof are provided according to the present invention.

The term "hydrophilic" is well-known in the art and refers to an antineoplastic chemotherapeutic that readily absorbs water and/or readily dissolves in water Ceramide anionic liposome compositions containing at least one vinca alkyloid antineoplastic chemotherapeutic and methods for use thereof are provided according to the present invention.

Vinca alkyloid antineoplastic chemotherapeutics are well-known in the art, see for example Remington: The Science and Practice of Pharmacy, Lippincott Williams & Wilkins, 21$^{st}$ ed., 2005, p. 437. Vinca alkyloid antineoplastic chemotherapeutics include, but are not limited to, vinblastine, vincristine, vinglycinate, vinorelbine and vindesine.

The term "liposome" refers to a bilayer particle of amphipathic lipid molecules enclosing an aqueous interior space. Liposomes are typically produced as small unilammellar vesicles (SUVs), large unilammellar vesicles (LUVs) or multilammellar vesicles (MLVs).

An antineoplastic chemotherapeutic is associated with liposomes by encapsulation in the aqueous interior space of the liposomes, disposed in the lipid bilayer of the liposomes and/or associated with the liposomes by binding, such as ionic binding or association by van der Waals forces. Liposomes according to aspects of the invention are generally in the range of about 1 nanometer—1 micron in diameter although they are not limited with regard to size.

Size of liposomes produced according to methods of the present invention can be controlled using well-known techniques, including, but not limited to, filtration through a filter having a defined pore size, extrusion and combinations thereof.

Ceramide anionic liposomes according to aspects of the present invention include C4 ceramide, C6 ceramide, C8 ceramide, C10 ceramide, C12 ceramide, C14 ceramide, C16 ceramide, C18 ceramide, or a combination of any two or more thereof, one or more types of neutral or cationic lipid and at least one type of anionic lipid, such that the ceramide anionic liposomes have a net negative charge at physiological pH. Preferably, a PEG-modified lipid (pegylated lipid) is included.

According to aspects of the present invention, C6 ceramide, C8 ceramide or both C6 ceramide and C8 ceramide are included in ceramide anionic liposomes of the present invention Ceramide anionic liposomes according to aspects of the present invention include, C6 ceramide (N-Hexanoyl-D-erythro-sphingosine), one or more types of neutral or cationic lipid and at least one type of anionic lipid, such that the ceramide anionic liposomes have a net negative charge at physiological pH. Preferably, a PEG-modified lipid (pegylated lipid) is included.

Ceramide anionic liposomes according to aspects of the present invention include, C8 ceramide (N-Octanoyl-D-erythro-Sphingosine), one or more types of neutral or cationic lipid and at least one type of anionic lipid, such that the ceramide anionic liposomes have a net negative charge at physiological pH. Preferably, a PEG-modified lipid (pegylated lipid) is included.

The term "cationic lipid" refers to any lipid which has a net positive charge at physiological pH. Examples of cationic lipids include, but are not limited to, N-(1-(2,3-dioleyloxy) propyl)-N,N,N-trimethylammonium chloride (DOTMA); 1,2-dioleoyloxy-3-(trimethylammonium)propane (DOTAP); 1,2-dioleoyl-3-dimethylammonium-propane (DODAP); dioctadecylamidoglycylspermine (DOGS); 1,2-dipalmitoylphosphatidylethanolamidospermine (DPPES); 2,3-dioleyloxy-N-(2-(sperminecarboxamido)ethyl)-N,N-dimethyl-1-propanaminium trifluoroacetate (DOSPA); dimyristoyltrimethylammonium propane (DMTAP); (3-dimyristyloxypropyl)(dimethyl)(hydroxyethyl)ammonium (DMRIE); dioctadecyldimethylammonium chloride (DODAC), Dimethyldidodecylammonium bromide (DDAB); 3β[N—(N',N'-dimethylaminoethane)-carbamoyl] cholesterol (DC-Chol); 1-[2-(9(Z)-octadecenoyloxy)-ethyl]-2-(8(Z)-heptadecenyl)-3-(2-hydroxyethyl)-imidazolinium (DOTIM); bis-guanidinium-spermidine-cholesterol (BGTC); bis-guanidinium-tren-cholesterol (BGTC); 1,3-Dioleoyloxy-2-(6-carboxy-spermyl)-propylamid (DOSPER) N-[3-[2-(1,3-dioleoyloxy)propoxy-carbonyl]propyl]-N,N, N-trimethylammonium iodide (YKS-220); as well as pharmaceutically acceptable salts and mixtures thereof. Additional examples of cationic lipids are described in Lasic and Papahadjopoulos, Medical Applications of Liposomes, Elsevier, 1998; U.S. Pat. Nos. 4,897,355; 5,208,036; 5,264, 618; 5,279,833; 5,283,185; 5,334,761; 5,459,127; 5,736,392; 5,753,613; 5,785,992; 6,376,248; 6,586,410; 6,733,777; and 7,145,039.

The term "neutral lipid" refers to any lipid which has no net charge, either uncharged or in neutral charge zwitterionic form, at physiological pH. Examples of neutral lipids include, but are not limited to, distearoylphosphatidylcholine (DSPC), dioleoylphosphatidylethanolamine (DOPE), distearoylphosphatidylethanolamine (DSPE); 1,2-dioleoyl-sn-glycero-3-

Phosphocholine (DOPC), cephalin, ceramide, cerebrosides, cholesterol, diacylglycerols, and sphingomyelin.

The term "anionic lipid" refers to any lipid which has a net negative charge at physiological pH. Examples of anionic lipids include, but are not limited to, dihexadecylphosphate (DhP), phosphatidyl inositols, phosphatidyl serines, such as dimyristoyl phosphatidyl serine, and dipalmitoyl phosphatidyl serine, phosphatidyl glycerols, such as dimyristoylphosphatidyl glycerol, dioleoylphosphatidyl glycerol, dilauryloylphosphatidyl glycerol, dipalmitoylphosphatidyl glycerol, distearyloylphosphatidyl glycerol, phosphatidic acids, such as dimyristoyl phosphatic acid and dipalmitoyl phosphatic acid and diphosphatidyl glycerol.

The total amount of anionic lipid included in ceramide anionic liposomes according to aspects of the present invention is an amount in the range of about 5-15 Molar percent, inclusive, more preferably an amount in the range of about 8-12 Molar percent, inclusive, still more preferably an amount in the range of about 9-11 Molar percent, inclusive, yet more preferably about 10 Molar percent.

The term "modified lipid" refers to lipids modified to aid in, for example, inhibiting aggregation and/or precipitation, inhibiting immune response and/or improving half-life in circulation in vivo. According to aspects of the present invention, the modified lipids are neutral lipids.

Modified neutral lipids include, but are not limited to, pegylated lipids, such as polyethyleneglycol 2000 distearoylphosphatidylethanolamine (PEG(2000) DSPE); and N-Octanoyl-Sphingosine-1-succinyl(methoxy(polyethylene)glycol)750 (abbreviated as PEG(750) C8 herein).

The total amount of pegylated neutral lipids included in ceramide anionic liposome compositions according to aspects of the present invention is an amount in the range of about 5-20 Molar percent, inclusive, more preferably in the range of about 8-12 Molar percent, inclusive, still more preferably in the range of about 9-11 Molar percent, inclusive, and yet more preferably about 10 Molar percent.

According to highly preferred aspects, N-Octanoyl-Sphingosine-1-succinyl(methoxy(polyethylene)glycol)750 (PEG(750) C8) is included in ceramide anionic liposome compositions of the present invention.

N-Octanoyl-Sphingosine-1-succinyl(methoxy(polyethylene)glycol)750 (PEG(750) C8) is included in ceramide anionic liposome compositions according to aspects of the present invention. The total amount of N-Octanoyl-Sphingosine-1-succinyl(methoxy(polyethylene)glycol)750 (PEG(750) C8) included in ceramide anionic liposome compositions according to aspects of the present invention is an amount in the range of about 5-20 Molar percent, inclusive, more preferably in the range of about 8-12 Molar percent, still more preferably in the range of about 9-11 Molar percent and yet more preferably about 10 Molar percent.

Two or more pegylated neutral lipids are included in ceramide anionic liposome compositions according to aspects of the present invention, wherein at least half of the amount of included total pegylated lipids is N-Octanoyl-Sphingosine-1-succinyl(methoxy(polyethylene)glycol)750 (PEG(750) C8).

Pegylated neutral lipids polyethyleneglycol 2000 distearoylphosphatidylethanolamine (PEG(2000) DSPE); and N-Octanoyl-Sphingosine-1-succinyl(methoxy(polyethylene)glycol)750 (PEG(750) C8) are included in ceramide anionic liposome compositions according to aspects of the present invention. The total amount of polyethyleneglycol 2000 distearoylphosphatidylethanolamine (PEG(2000) DSPE) and N-Octanoyl-Sphingosine-1-succinyl(methoxy(polyethylene)glycol)750 (PEG(750) C8) included in ceramide anionic liposome compositions according to aspects of the present invention is an amount in the range of about 5-20 Molar percent, inclusive, more preferably in the range of about 8-12 Molar percent, inclusive, still more preferably in the range of about 9-11 Molar percent, inclusive, and yet more preferably about 10 Molar percent.

C6 ceramide is included in ceramide anionic liposome compositions according to aspects of the present invention is an amount in the range of about 1-40 Molar percent, inclusive, more preferably in the range of about 5-38 Molar percent, inclusive, still more preferably in the range of about 10-35 Molar percent, inclusive. According to aspects of the present invention, C6 ceramide is included in ceramide anionic liposome compositions is an amount of about 30 Molar percent. The C6 ceramide is not pegylated.

C8 ceramide is included in ceramide anionic liposome compositions according to aspects of the present invention is an amount in the range of about 1-40 Molar percent, inclusive, more preferably in the range of about 5-38 Molar percent, inclusive, still more preferably in the range of about 10-35 Molar percent, inclusive. According to aspects of the present invention, C8 ceramide is included in ceramide anionic liposome compositions is an amount of about 30 Molar percent. Thus, C8 ceramide (N-Octanoyl-D-erythro-Sphingosine), which has anti-cancer activity, and polyethyleneglycol 750 C8 ceramide (N-Octanoyl-Sphingosine-1-succinyl(methoxy(polyethylene)glycol)750, also called PEG(750) C8 herein), which has substantially no anti-cancer activity compared to N-Octanoyl-D-erythro-Sphingosine, are both included in liposomes according to aspects of the present invention, According to aspects of the present invention, the amount of C4-C18 ceramide, preferably C6 ceramide and/or C8 ceramide, included in the ceramide anionic liposomes may be varied in proportion to the amount of hydrophilic antineoplastic chemotherapeutic to be encapsulated in the ceramide anionic liposomes such that the ratio of the C4-C18 ceramide, preferably C6 ceramide and/or C8 ceramide to hydrophilic antineoplastic chemotherapeutic is in the range of about 1:10-10:1.

Particular ratios of components included in liposomes according to aspects of the present invention are neutral lipid: modified neutral lipid:anionic lipid:C4-C18 ceramide—3-5.5 neutral lipid:1-4 modified neutral lipid:1 anionic lipid:3 C4-C18 ceramide.

Particular ratios of components included in liposomes according to aspects of the present invention are neutral lipid: modified neutral lipid:anionic lipid: C4-C18 ceramide—3:4:1:3.

Particular ratios of components included in liposomes according to aspects of the present invention are neutral lipid: modified neutral lipid:anionic lipid: C4-C18 ceramide—4.5:2:1:3.

Particular ratios of components included in liposomes according to aspects of the present invention are neutral lipid: modified neutral lipid:anionic lipid: C4-C18 ceramide—4.5:1.5:1:3.

Thus, according to preferred aspects, ceramide anionic liposome compositions of the present invention include at least one modified neutral lipid, wherein the total amount of modified neutral lipid is an amount in the range of about 5-20 Molar percent, inclusive, more preferably in the range of about 8-12 Molar percent, still more preferably in the range of about 9-11 Molar percent and yet more preferably about 10 Molar percent, wherein at least half of the amount of included modified neutral lipid is N-Octanoyl-Sphingosine-1-succinyl(methoxy(polyethylene)glycol)750 (PEG(750) C8); at least one anionic lipid, wherein the total amount of anionic lipid is an amount in the range of about 5-20 Molar percent, inclusive, more preferably in the range of about 8-12 Molar percent, still more preferably in the range of about 9-11 Molar percent and yet more preferably about 10 Molar percent; C4-C18 ceramide in an amount in the range of 1-40 Molar percent, inclusive, more preferably in the range of about 5-38 Molar percent, inclusive, still more preferably in the range of about 10-35 Molar percent, inclusive, more preferably 30 Molar percent; and further including cationic or neutral lipids, with the proviso that the resulting ceramide anionic liposome compositions have a net negative charge at physiological pH.

Thus, according to highly preferred aspects, ceramide anionic liposome compositions of the present invention include at least one pegylated neutral lipid, wherein the total amount of pegylated neutral lipid is an amount in the range of about 5-20 Molar percent, inclusive, more preferably in the range of about 8-12 Molar percent, still more preferably in the range of about 9-11 Molar percent and yet more preferably about 10 Molar percent, wherein at least half of the amount of included modified neutral lipid is N-Octanoyl-Sphingosine-1-succinyl(methoxy(polyethylene)glycol)750 (PEG(750) C8); at least one anionic lipid, wherein the total amount of anionic lipid is an amount in the range of about 5-20 Molar percent, inclusive, more preferably in the range of about 8-12 Molar percent, still more preferably in the range of about 9-11 Molar percent and yet more preferably about 10 Molar percent; C4-C18 ceramide in an amount in the range of 1-40 Molar percent, inclusive, more preferably in the range of about 5-38 Molar percent, inclusive, still more preferably in the range of about 10-35 Molar percent, inclusive, more preferably 30 Molar percent; and further including cationic or neutral lipids, with the proviso that the resulting ceramide anionic liposome compositions have a net negative charge at physiological pH.

The term "Molar percent" as used herein to refer to amounts of C4-C18 ceramide and neutral, anionic, cationic and modified lipids included in ceramide anionic liposome compositions of the present invention, refers to the amount of the particular component as a Molar percent of total lipids in the ceramide anionic liposome compositions, excluding any antineoplastic chemotherapeutic contained in the liposomes.

Ceramide anionic liposome compositions containing one or more hydrophilic antineoplastic chemotherapeutics are provided according to aspects of the present invention.

Ceramide anionic liposome compositions containing one or more vinca alkyloids are provided according to aspects of the present invention.

Ceramide anionic liposome compositions containing vinblastine, vincristine, vinglycinate, vinorelbine, vindesine, cladribine, sorafenib; or a combination of any two or more thereof are provided according to aspects of the present invention.

In addition to containing one or more hydrophilic antineoplastic chemotherapeutics and/or one or more vinca alkyloids, ceramide anionic liposome compositions of the present invention optionally contain any of a variety of useful biologically active molecules and substances including, but not limited to, proteins, peptides, carbohydrates, oligosaccharides, drugs, and nucleic acids capable of being complexed with the liposomes. The term "biologically active molecules and substances" refers molecules or substances that exert a biological effect in vitro and/or in vivo, such as, but not limited to, nucleic acids, inhibitory RNA, siRNA, shRNA, ribozymes, antisense nucleic acids, antibodies, hormones, small molecules, aptamers, decoy molecules and toxins.

Methods and compositions are provided according to the present invention for treating cancer.

Methods of treatment of a subject having, or at risk of having, cancer, are provided according to aspects of the present invention including administration of a pharmaceutically effective amount of a ceramide anionic liposome composition containing one or more antineoplastic chemotherapeutics.

Methods of treatment of a subject having, or at risk of having, cancer, are provided according to aspects of the present invention including administration of a pharmaceutically effective amount of a ceramide anionic liposome composition containing one or more vinca alkyloids Methods of treatment of a subject having, or at risk of having, cancer, are provided according to aspects of the present invention including administration of a pharmaceutically effective amount of a ceramide anionic liposome composition containing vinblastine, vincristine, vinglycinate, vinorelbine, vindesine, cladribine, sorafenib; or a combination of any two or more thereof.

Particular cancers treated using methods and compositions of the present invention are characterized by abnormal cell proliferation including, but not limited to, pre-neoplastic hyperproliferation, cancer in-situ, neoplasms and metastasis. Cancers treated using methods and compositions of the present invention include solid tumors including, but not limited to, cancers of the head and neck, esophagus, rectum, anus, prostate, testicle, lung, pancreas, bladder, ovary, uterus, cervix, thyroid, breast, colon, kidney, liver, brain and skin, as well as non-solid tumors, including, but not limited to, hematological malignancies such as leukemia, lymphoma and multiple myeloma. Methods and compositions of the present invention can be used for prophylaxis as well as amelioration of signs and/or symptoms of cancer.

The terms "treating" and "treatment" used to refer to treatment of a cancer in a subject include: preventing, inhibiting or ameliorating the cancer in the subject, such as slowing progression of the cancer and/or reducing or ameliorating a sign or symptom of the cancer.

A therapeutically effective amount of a composition of the present invention is an amount which has a beneficial effect in a subject being treated. In subjects having cancer or at risk for having cancer, such as a condition characterized by abnormal cell proliferation including, but not limited to, pre-neoplastic hyperproliferation, cancer in-situ, neoplasms, metastasis, a tumor, a benign growth or other condition responsive to a composition of the present invention, a therapeutically effective amount of a composition of the present invention is effective to ameliorate or prevent one or more signs and/or symptoms of the condition. For example, a therapeutically effective amount of a composition of the present invention is effective to detectably increase apoptosis and/or decrease proliferation of cells of a cancer condition characterized by abnormal cell proliferation including, but not limited to, pre-neoplastic hyperproliferation, cancer in-situ, neoplasms, metastasis, a tumor, a benign growth or other condition responsive to a composition of the present invention.

A subject treated according to methods and using compositions of the present invention can be mammalian or non-mammalian. A mammalian subject can be any mammal including, but not limited to, a human; a non-human primate; a rodent such as a mouse, rat, or guinea pig; a domesticated pet such as a cat or dog; a horse, cow, pig, sheep, goat, or rabbit. A non-mammalian subject can be any non-mammal including, but not limited to, a bird such as a duck, goose, chicken, or turkey. In aspects of methods including administration of an inventive pharmaceutical composition to a subject, the subject is human.

Optionally, methods of the present invention additionally include administration of one or more adjunct pharmacologically active agents.

Non-limiting examples of adjunct pharmacologically active agents that can be administered according to aspects of methods of the present invention include non-steroidal anti-inflammatory agents, antibiotics, antivirals, analgesics, antipyretics, antidepressants, antipsychotics, anticancer agents, antihistamines, anti-osteoporosis agents, anti-osteonecrosis agents, antiinflammatory agents, anxiolytics, chemotherapeutic agents, diuretics, growth factors, hormones and vasoactive agents.

Optionally, a method of treating a subject having cancer or at risk of having cancer further includes an adjunct anti-cancer treatment. An adjunct anti-cancer treatment can be administration of one or more additional antineoplastic chemotherapeutic agents, included or not included in inventive liposomes, administered separately or together.

A therapeutically effective amount of a pharmaceutical composition of ceramide anionic liposomes encapsulating a hydrophilic antineoplastic chemotherapeutic according to the present invention will vary depending on the particular pharmaceutical composition used, the severity of the condition to be treated, the species of the subject, the age and sex of the subject and the general physical characteristics of the subject to be treated. One of skill in the art could determine a therapeutically effective amount in view of these and other considerations typical in medical practice. In general it is contemplated that a therapeutically effective amount would be in the range of about 0.001 mg/kg-100 mg/kg body weight, optionally in the range of about 0.01-10 mg/kg, and further optionally in the range of about 0.1-5 mg/kg. Further, dosage may be adjusted depending on whether treatment is to be acute or continuing.

Antineoplastic chemotherapeutics are described, for example, in Goodman et al., Goodman and Gilman's The Pharmacological Basis of Therapeutics, 8th Ed., Macmillan Publishing Co., 1990.

Antineoplastic chemotherapeutics illustratively include acivicin, aclarubicin, acodazole, acronine, adozelesin, aldesleukin, alitretinoin, allopurinol, altretamine, ambomycin, ametantrone, amifostine, aminoglutethimide, amsacrine, anastrozole, anthramycin, arsenic trioxide, asparaginase, asperlin, azacitidine, azetepa, azotomycin, batimastat, benzodepa, bicalutamide, bisantrene, bisnafide dimesylate, bizelesin, bleomycin, brequinar, bropirimine, busulfan, cactinomycin, calusterone, capecitabine, caracemide, carbetimer, carboplatin, carmustine, carubicin, carzelesin, cedefingol, celecoxib, chlorambucil, cirolemycin, cisplatin, cladribine, crisnatol mesylate, cyclophosphamide, cytarabine, dacarbazine, dactinomycin, daunorubicin, decitabine, dexormaplatin, dezaguanine, dezaguanine mesylate, diaziquone, docetaxel, doxorubicin, droloxifene, dromostanolone, duazomycin, edatrexate, eflornithine, elsamitrucin, enoplatin, enpromate, epipropidine, epirubicin, erbulozole, esorubicin, estramustine, etanidazole, etoposide, etoprine, fadrozole, fazarabine, fenretinide, floxuridine, fludarabine, fluorouracil, flurocitabine, fosquidone, fostriecin, fulvestrant, gemcitabine, hydroxyurea, idarubicin, ifosfamide, ilmofosine, interleukin II (IL-2, including recombinant interleukin II or rIL2), interferon alfa-2a, interferon alfa-2b, interferon alfa-n1, interferon alfa-n3, interferon beta-Ia, interferon gamma-Ib, iproplatin, irinotecan, lanreotide, letrozole, leuprolide, liarozole, lometrexol, lomustine, losoxantrone, masoprocol, maytansine, mechlorethamine hydrochlride, megestrol, melengestrol acetate, melphalan, menogaril, mercaptopurine, methotrexate, metoprine, meturedepa, mitindomide, mitocarcin, mitocromin, mitogillin, mitomalcin, mitomycin, mitosper, mitotane, mitoxantrone, mycophenolic acid, nelarabine, nocodazole, nogalamycin, ormnaplatin, oxisuran, paclitaxel, pegaspargase, peliomycin, pentamustine, peplomycin, perfosfamide, pipobroman, piposulfan, piroxantrone hydrochloride, plicamycin, plomestane, porfimer, porfiromycin, prednimustine, procarbazine, puromycin, pyrazofurin, riboprine, rogletimide, safingol, semustine, simtrazene, sorafenib, sparfosate, sparsomycin, spirogermanium, spiromustine, spiroplatin, streptonigrin, streptozocin, sulofenur, talisomycin, tamoxifen, tecogalan, tegafur, teloxantrone, temoporfin, teniposide, teroxirone, testolactone, thiamiprine, thioguanine, thiotepa, tiazofurin, tirapazamine, topotecan, toremifene, trestolone, triciribine, trimetrexate, triptorelin, tubulozole, uracil mustard, uredepa, vapreotide, verteporfin, vinblastine, vincristine sulfate, vindesine, vinepidine, vinglycinate, vinleurosine, vinorelbine, vinrosidine, vinzolidine, vorozole, zeniplatin, zinostatin, zoledronate, and zorubicin.

An adjunct anti-cancer treatment can be a radiation treatment of a subject or an affected area of a subject's body.

Hydrophilic antineoplastic chemotherapeutics are well-known in the art, including, but not limited to, vinblastine, vincristine, vinglycinate, vinorelbine, vindesine, sorafenib and cladribine.

Vinblastine is a well-known antineoplastic chemotherapeutic currently used in treatment of non-Hodgkin's lymphoma, small cell lung cancer, head and neck cancer, testicular cancers, breast cancers and various germ-cell cancers and compositions of the present invention may be used to treat these and other cancers. Vincristine is a well-known antineoplastic chemotherapeutic currently used in treatment of acute lymphocytic luekemias, multiple myelomas, rhabdomyosarcomas, neuroblastomas, Ewings sarcoma and Wilm's tumor and compositions of the present invention may be used to treat these and other cancers. Cladribine is a well-known antineoplastic chemotherapeutic currently used to treat hairy cell leukemias and compositions of the present invention may be used to treat these and other cancers. Sorafenib is a well-known antineoplastic chemotherapeutic currently used to treat renal cell carcinomas and hepatocellular carcinomas and compositions of the present invention may be used to treat these and other cancers. Vinorelbine is a well-known antineoplastic chemotherapeutic currently used to treat breast cancers and non-small cell lung cancers and compositions of the present invention may be used to treat these and other cancers. Vindesine is a well-known antineoplastic chemotherapeutic currently used to treat leukemias, lymphomas, melanomas, breast cancers and lung cancers and compositions of the present invention may be used to treat these and other cancers. Vinglycinate is a well-known antineoplastic chemotherapeutic currently used in treatment of Hodgkin's disease, lymphosarcomas, lung cancers and chondrosarcomas and compositions of the present invention may be used to treat these and other cancers.

Methods of the present invention include administration of ceramide anionic liposomes encapsulating one or more hydrophilic antineoplastic chemotherapeutics as pharmaceutical formulations, including those suitable for oral, rectal, nasal, pulmonary, epidural, ocular, otic, intraarterial, intracardiac, intracerebroventricular, intradermal, intravenous, intramuscular, intraperitoneal, intraosseous, intrathecal, intravesical, subcutaneous, topical, transdermal, and transmucosal, such as by sublingual, buccal, vaginal, and inhalational, routes of administration.

Compositions including a hydrophilic antineoplastic chemotherapeutic encapsulated in ceramide anionic liposomes according to the present invention may be administered directly or may be formulated with one or more additional pharmaceutically acceptable carriers where desired. The term "pharmaceutically acceptable carrier" refers to a carrier which is substantially non-toxic to a subject to which the composition is administered and which is substantially chemically inert with respect to ceramide anionic liposomes and the encapsulated antineoplastic therapeutic of the present invention. Pharmaceutically acceptable carriers and formulation of pharmaceutical compositions are known in the art, illustratively including, but not limited to, as described in Remington: The Science and Practice of Pharmacy, 21st Ed., Lippincott, Williams & Wilkins, Philadelphia, Pa., 2006; and Allen, L. V. et al., Ansel's Pharmaceutical Dosage Forms and Drug Delivery Systems, 8th Ed., Lippincott, Williams & Wilkins, Philadelphia, Pa., 2005.

Pharmaceutical compositions suitable for delivery to a subject may be prepared in various forms illustratively including physiologically acceptable sterile aqueous or nonaqueous solutions, dispersions, suspensions or emulsions, and sterile powders for reconstitution into sterile injectable solutions or dispersions. Examples of suitable aqueous and nonaqueous carriers include water, ethanol, polyols such as propylene glycol, polyethylene glycol, glycerol, and the like, suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate. Additional components illustratively including a buffer, a solvent, or a diluent may be included.

Such formulations are administered by a suitable route including parenteral and oral administration. Administration may include systemic or local injection, and particularly intravenous injection.

These compositions may also contain adjuvants such as preserving, wetting, emulsifying, and dispensing agents. Prevention of the action of microorganisms can be ensured by various antibacterial and antifungal agents, for example, parabens, chlorobutanol, phenol, sorbic acid, and the like. It may also be desirable to include isotonic agents, for example, sugars, sodium chloride, and substances similar in nature. Prolonged delivery of an injectable pharmaceutical form can be brought about by the use of agents delaying absorption, for example, aluminum monostearate and gelatin.

Solid dosage forms for oral administration include capsules, tablets, pills, powders, and granules. In such solid dosage forms, at least one inert customary excipient (or carrier) can be included such as sodium citrate or dicalcium phosphate or (a) fillers or extenders, as for example, starches, lactose, sucrose, glucose, mannitol, and silicic acid, (b) binders, as for example, carboxymethylcellulose, alignates, gelatin, polyvinylpyrrolidone, sucrose, and acacia, (c) humectants, as for example, glycerol, (d) disintegrating agents, as for example, agar-agar, calcium carbonate, plant starches such as potato or tapioca starch, alginic acid, certain complex silicates, and sodium carbonate, (e) solution retarders, as for example, paraffin, (f) absorption accelerators, as for example, quaternary ammonium compounds, (g) wetting agents, as for example, cetyl alcohol, glycerol monostearate, and glycols (h) adsorbents, as for example, kaolin and bentonite, and (i) lubricants, as for example, talc, calcium stearate, magnesium stearate, solid polyethylene glycols, sodium lauryl sulfate, or mixtures thereof. In the case of capsules, tablets, and pills, the dosage forms may also include a buffering agent.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

Liquid dosage forms for oral administration include a pharmaceutically acceptable carrier formulated as an emulsion, solution, suspension, syrup, or elixir. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and the like.

Besides such inert diluents, the composition can also include adjuvants, such as wetting agents, emulsifying and suspending agents, sweetening, flavoring, and perfuming agents.

Suspensions, in addition to a hydrophilic antineoplastic chemotherapeutic encapsulated in ceramide anionic liposomes, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and the like.

A topical formulation can be an ointment, lotion, cream or gel in particular aspects. Topical dosage forms such as ointment, lotion, cream or gel bases are described in Remington: The Science and Practice of Pharmacy, 21st Ed., Lippincott Williams & Wilkins, 2006, p. 880-882 and p. 886-888; and in Allen, L. V. et al., Ansel's Pharmaceutical Dosage Forms and Drug Delivery Systems, 8th Ed., Lippincott Williams & Wilkins, 2005, p. 277-297.

A pharmaceutical composition according to the invention generally includes about 0.1-99% ceramide anionic liposomes encapsulating a hydrophilic antineoplastic therapeutic. Combinations of two or more populations of ceramide anionic liposomes encapsulating different hydrophilic antineoplastic therapeutics in a pharmaceutical composition are also considered within the scope of the present invention.

Methods of producing ceramide anionic liposomes containing one or more hydrophilic antineoplastic chemotherapeutics encapsulated in the interior space of the anionic liposomes are provided according to the present invention.

Methods of producing ceramide anionic liposomes containing one or more hydrophilic vinca alkyloid antineoplastic chemotherapeutics encapsulated in the interior space of the anionic liposomes are provided according to the present invention.

Methods of producing ceramide anionic liposomes containing one or more antineoplastic chemotherapeutics containing one or more of: vinblastine, vincristine, vinglycinate, vinorelbine, vindesine, sorafenib and cladribine, encapsulated in the interior space of the ceramide anionic liposomes are provided according to the present invention.

Preparation of the ceramide anionic liposomes encapsulating one or more hydrophilic antineoplastic chemotherapeutics is performed with special reference to temperatures used, in contrast to previous methods. In particular, an extrusion step is performed at a temperature in the range of 67-75 degrees Celsius, inclusive, more preferably in the range of 67-69 degrees Celsius, inclusive, and most preferably at 68 degrees Celsius. The steps of rehydrating the lipid mixture in an aqueous pharmaceutically acceptable liquid characterized by physiological pH, and the first and second sonication steps are performed at a temperature in the range of 55-75 degrees Celsius, inclusive, more preferably 60-70 degrees Celsius, inclusive, and most preferably at 65 degrees Celsius. This "trapping" mechanism of encapsulation that uses temperature instead of traditional pH-based methodologies to achieve formation of pharmaceutical formulations of ceramide anionic liposomes containing a therapeutic dose of vinca alkyloids and other hydrophilic antineoplastic chemotherapeutics, avoiding premature degradation of the vinca alkyloids and other hydrophilic antineoplastic chemotherapeutics.

The phrase "aqueous pharmaceutically acceptable liquid" with reference to "rehydration" of a lipid mixture according to aspects of the present invention refers to a liquid which is substantially non-toxic to a subject and which is substantially chemically inert with respect to the lipids and the antineoplastic chemotherapeutic to be encapsulated. A non-limiting example is phosphate buffered saline/normal saline.

Methods of producing a pharmaceutical composition are provided according to aspects of the present invention which include providing a lipid mixture comprising: at least one pegylated neutral lipid, wherein the total amount of pegylated neutral lipid is an amount in the range of 5-20 Molar percent, inclusive, of the total lipid mixture and wherein at least half of the amount of included pegylated neutral lipid is N-Octanoyl-Sphingosine-1-succinyl(methoxy(polyethylene)glycol)750 (PEG(750) C8); at least one anionic lipid, wherein the total amount of anionic lipid is an amount in the range of 5-15 Molar percent, inclusive, of the total lipid mixture; C6 ceramide in an amount in the range of 1-40 Molar percent, inclusive, of the total lipid mixture; and cationic or neutral lipids, with the proviso that the resulting lipid mixture has a net negative charge at physiological pH. The lipid mixture is dried to remove solvents under nitrogen and then suspended in an aqueous pharmaceutically acceptable liquid. A hydrophilic antineoplastic chemotherapeutic is added to the lipid mixture suspended in the aqueous pharmaceutically acceptable buffer such that the ratio of the amount of the hydrophilic antineoplastic chemotherapeutic to the amount of total lipids in the suspended lipid mixture is in the range of about 1:1-1:100. The combination of lipids and drug is then sonicated at a temperature in the range of 55-75 degrees Celsius, inclusive, to produce a sonicated mixture. The sonicated mixture is then passed through a filter having pores of a desired size to produce liposomes having the desired size, at a temperature in the range of 67-75 degrees Celsius, producing a population of ceramide anionic liposomes, wherein the population of ceramide anionic liposomes contains greater than 10%, greater than 25% or greater than 50% of the amount of the hydrophilic antineoplastic chemotherapeutic added to the lipid mixture, encapsulated in the aqueous core of the liposomes.

Methods of producing a pharmaceutical composition are provided according to aspects of the present invention which include providing a lipid mixture comprising: at least one pegylated neutral lipid, wherein the total amount of pegylated neutral lipid is an amount in the range of 5-20 Molar percent, inclusive, of the total lipid mixture and wherein at least half of the amount of included pegylated neutral lipid is N-Octanoyl-Sphingosine-1-succinyl(methoxy(polyethylene)glycol)750 (PEG(750) C8); at least one anionic lipid, wherein the total amount of anionic lipid is an amount in the range of 5-15 Molar percent, inclusive, of the total lipid mixture; C6 ceramide in an amount in the range of 1-40 Molar percent, inclusive, of the total lipid mixture; and cationic or neutral lipids, with the proviso that the resulting lipid mixture has a net negative charge at physiological pH. The lipid mixture is dried to remove solvents under nitrogen and then suspended in an aqueous pharmaceutically acceptable liquid. A hydrophilic antineoplastic chemotherapeutic is added to the lipid mixture suspended in the aqueous pharmaceutically acceptable buffer such that the ratio of the amount of the hydrophilic antineoplastic chemotherapeutic to the amount of total lipids in the suspended lipid mixture is in the range of about 1:1-1:100. The combination of lipids and drug is then sonicated at a temperature in the range of 55-75 degrees Celsius, inclusive, to produce a sonicated mixture. The sonicated mixture is then passed through a filter having pores of a desired size to produce liposomes having the desired size, at a temperature in the range of 67-75 degrees Celsius, producing a population of ceramide anionic liposomes, wherein the population of ceramide anionic liposomes contains greater 15-75% of the amount of the hydrophilic antineoplastic chemotherapeutic added to the lipid mixture, encapsulated in the aqueous core of the liposomes.

Commercial Packages

Commercial packages are provided according to aspects of the present invention for treating cancer in a subject in need thereof, including one or more hydrophilic antineoplastic chemotherapeutics encapsulated in ceramide anionic liposomes. One or more auxiliary components are optionally included in commercial packages of the present invention, such as a pharmaceutically acceptable carrier exemplified by a buffer or diluent.

Aspects of inventive compositions and methods are illustrated in the following examples. These examples are provided for illustrative purposes and are not considered limitations on the scope of inventive compositions and methods.

EXAMPLES

Example 1

Table I shows amounts of the indicated materials included in liposomes used in this example.

TABLE I

| Lipid | MW (mg/mmol) | Mg Lipid | μmol | Molar Ratio | Stock (mg/ml) | μl (1 ml) |
|---|---|---|---|---|---|---|
| DSPC | 790.16 | 9.0746 | 11.4845 | 3.75 | 25 | 362.98 |
| DOPE | 744.04 | 3.9876 | 5.3594 | 1.75 | 25 | 159.51 |
| PEG(2000)-DSPE | 2805.54 | 4.2960 | 1.5313 | 0.5 | 25 | 171.84 |
| PEG(750)-C8 | 1244.64 | 1.9059 | 1.5313 | 0.5 | 25 | 76.23 |
| Dihexadecyl Phosphate | 546.86 | 2.4138 | 4.4140 | 1 | 25 | 96.55 |
| C6-Cer | 397.64 | 3.1160 | 7.8361 | 3 | 25 | 124.64 |
| Total | x | 24.7939 | 32.1565 | 10.5 | 25 | 991.76 |

Abbreviations for Table I: DSPC, distearoylphosphatidylcholine; DOPE dioleoylphosphatidylethanolamine; PEG (2000) DSPE, polyethyleneglycol 2000 distearoylphosphatidylethanolamine; PEG(750) C8, N-Octanoyl-Sphingosine-1-succinyl(methoxy(polyethylene)glycol)750; C6-cer, C6 ceramide.

Methods according to aspects of the present invention for making hydrophilic antineoplastic chemotherapeutic-containing ceramide anionic liposomes allow achievement of high encapsulation efficiencies with a stable anionic nanoscale liposome formulation. The lipids to be included in the liposomes are combined in a mixture, dried under nitrogen to remove solvents and then rehydrated in PBS/normal saline at 65 degrees Celsius for up to 3 hours, followed by sonication for two minutes. In this example, five milligrams vinblastine in 100 microliters of phosphate buffered saline/0.9% NaCl is added to 900 microliters of the lipid mixture such that the vinblastine concentration is 5 mg/mL and the vinblastine:lipid ratio is 5 mg drug:24.79 mg lipid, followed by overnight incubation (12-18 hrs) at room temperature. After the overnight incubation, the mixture was warmed to 65 degrees Celsius for 30 minutes, followed by a second sonication at 65 degrees Celsius for 5 minutes until translucent and then extrusion at 68 degrees Celsius using a 100 nM filter within a miniextruder (9 passages), producing a "final product" of 90 nanometer sized ceramide anionic liposomes including 28.5 molar percent short chain ceramide, 9.5 molar percent pegylated shell and 9.5 molar percent anionic dihexadecyl phosphate which allows for encapsulation in the void volume of the liposome of between 3 to 4 mg of vinblastine from an initial concentration of 5 mg/ml. These values are determined by LC/MS methodologies and reveal no premature degradation of the vinblastine as a function of encapsulation. These encapsulation efficiencies of nearly 75% are the result of using the anionic formulations described herein. Without inclusion of anionic lipid in liposomes as described herein, efficiencies of encapsulation of vinblastine are below 10% and the resulting liposomes are highly unstable. These final products produced in this Example encapsulate a therapeutic molar dose of vinblastine of 4 mM within ceramide anionic liposomes containing 8.8 µM ceramide.

The final product was run through a CL-4B sepharose column to remove free vinblastine. Final products are stored at room temperature.

These nanoscale preparations of 90 nm sized liposomes are stable for at least 2 months as evidenced by a lack of change in size (FIG. 1) and zeta potential charge measurements. Specifically, the dynamic light scattering measurements do not change as a function of time (7,14, 21 days).

Biological evidence of combinatorial efficacy of the ceramide anionic anionic liposomes encapsulating vinblastine includes cell respiration/survival data, in which a synergistic effect of the combinatorial ceramide/vinblastine product is observed compared to either agent alone in pancreatic tumor cells. Panc 1 pancreatic cancer cells were treated with 3.2 µM anionic (A) and neutral ceramide (C6) or non-ceramide nanoliposomes that either contained 0.01, 0.1 or 1 µM vinblastine or PBS. Ghost liposomes contained no ceramide or vinblastine. Unencapsulated (free) vinblastine was also administered at similar concentrations. All treatments were for 24 hrs.

Cell viability was assessed by MTS assay, which measures cellular respiration as a function of reduction of MTS to formazene at 490 nm. Only the high concentration of free vinblastine reduced cell viability. Ceramide nanolipsomes had minimal affects upon cellular viability. In contrast, the ceramide anionic/vinblastine nanoliposome had significant affects upon cellular viability. One way ANOVA revealed a p<0.05 statistical difference between free vinblastine and the encapsulated vinblastine within a ceramide nanoliposome. N=6 individual samples for each condition, replicated in triplicate.

Figure 2:
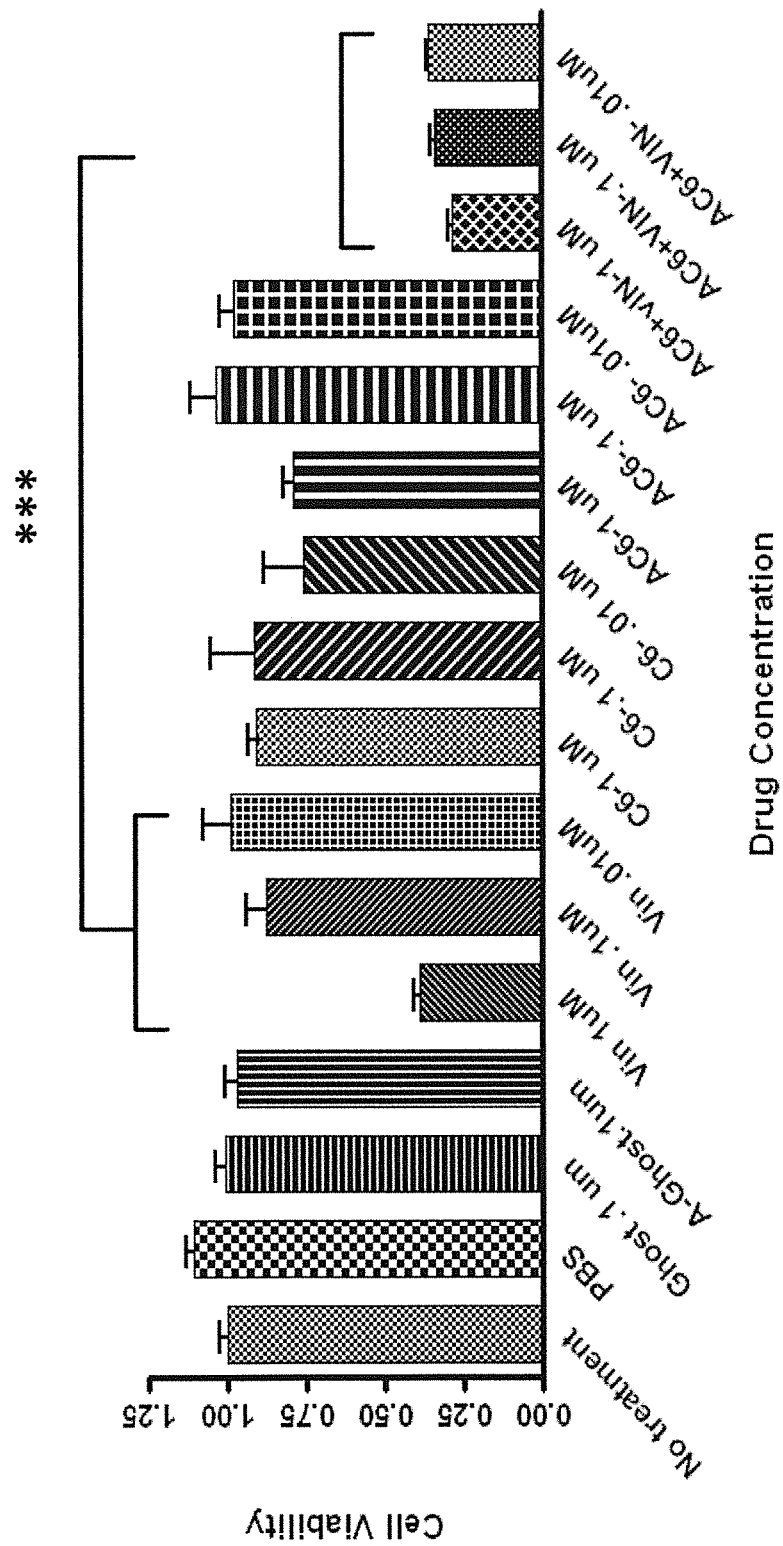
FIG. 2 is a graph showing effects of ceramide anionic liposome compositions of the present invention including vinblastine in a tumor model.

FIG. 2 is a graph showing data from these experiments showing that formulated C6 ceramide/vinblastine nanoliposomes are efficacious in a tumor model as compared to either C6 ceramide nanoliposomes or vinblastine alone. Abbreviations used in FIG. 2: PBS:Phosphate buffered Saline; Ghost: neutral liposome (no ceramide); AC6:Anionic C6 liposome; Vin: Vinblastine alone; C6:Neutral C6 ceramide; liposome A-Ghost:Anionic liposome (no ceramide); AC6+ VIN:Ceramide anionic liposome that contains vinblastine.

Similar procedures are followed using hydrophilic antineoplastic chemotherapeutic drugs, such as sorafenib and cladribine, or other vinca alkyloids such as vincristine, vinglycinate, vinorelbine and vindesine, to obtain similar drug loading and anti-cancer effects.

Example 2

Table II shows amounts of the indicated materials included in liposomes used in this example.

TABLE II

| Lipid | MW (mg/ mmol) | Mg Lipid | µmol | Molar Ratio | Stock (mg/ml) | µl (1 ml) |
|---|---|---|---|---|---|---|
| DSPC | 790.16 | 7.2212 | 9.1389 | 2.75 | 25 | 288.85 |
| DOPE | 744.04 | 4.3271 | 5.8156 | 1.75 | 25 | 173.08 |
| PEG(2000)-DSPE | 2805.54 | 6.9926 | 2.4924 | 0.75 | 25 | 279.70 |
| PEG(750)-C8 | 1244.64 | 3.1022 | 2.4924 | 0.75 | 25 | 124.09 |
| Dihexadecyl Phosphate | 546.86 | 2.4138 | 4.4140 | 1 | 25 | 96.55 |
| C6-Cer | 397.64 | 3.5306 | 8.8789 | 3 | 25 | 141.22 |
| Total | x | 27.5874 | 33.2322 | 10 | 25 | 1103.50 |

Abbreviations for Table II: DSPC, distearoylphosphatidylcholine; DOPE dioleoylphosphatidylethanolamine; PEG (2000) DSPE, polyethyleneglycol 2000 distearoylphosphatidylethanolamine; PEG(750) C8, N-Octanoyl-Sphingosine-1-succinyl(methoxy(polyethylene)glycol)750; C6-Cer, C6 ceramide.

Liposomes are made according to the procedure described in Example 1 using the materials and amounts listed in Table II to produce ceramide anionic liposomes including one or more encapsulated hydrophilic antineoplastic chemotherapeutic drugs, such as sorafenib and cladribine, or other vinca alkyloids such as vincristine, vinglycinate, vinorelbine and vindesine, to obtain similar drug loading and anti-cancer effects.

Example 3

Table III shows amounts of the indicated materials included in liposomes used in this example.

TABLE III

| Lipid | MW (mg/ mmol) | Mg Lipid | µmol | Molar Ratio | Stock (mg/ml) | µl (1 ml) |
|---|---|---|---|---|---|---|
| DSPC | 790.16 | 6.9263 | 8.7657 | 2.75 | 25 | 277.05 |
| DOPE | 744.04 | 4.1504 | 5.5782 | 1.75 | 25 | 166.02 |
| PEG(2000)-DSPE | 2805.54 | 8.9427 | 3.1875 | 1 | 25 | 357.71 |

TABLE III-continued

| Lipid | MW (mg/mmol) | Mg Lipid | μmol | Molar Ratio | Stock (mg/ml) | μl (1 ml) |
|---|---|---|---|---|---|---|
| PEG(750)-C8 | 1244.64 | 3.9673 | 3.1875 | 1 | 25 | 158.69 |
| Dihexadecyl Phosphate | 546.86 | 2.4138 | 4.4140 | 1 | 25 | 96.55 |
| C6-Cer | 397.64 | 3.3148 | 8.3361 | 3 | 25 | 132.59 |
| Total | x | 29.7154 | 33.4690 | 10.5 | 25 | 1188.61 |

Abbreviations for Table III: DSPC, distearoylphosphatidylcholine; DOPE dioleoylphosphatidylethanolamine; PEG (2000) DSPE, polyethyleneglycol 2000 distearoylphosphatidylethanolamine; PEG(750) C8, N-Octanoyl-Sphingosine-1-succinyl(methoxy(polyethylene)glycol)750; C6-Cer, C6 ceramide.

Liposomes are made according to the procedure described in Example 1 using the materials and amounts listed in Table III to produce ceramide anionic liposomes including one or more encapsulated hydrophilic antineoplastic chemotherapeutic drugs, such as sorafenib and cladribine, or other vinca alkyloids such as vincristine, vinglycinate, vinorelbine and vindesine, to obtain similar drug loading and anti-cancer effects.

Example 4

Table IV shows amounts of the indicated materials included in liposomes used in this example.

TABLE IV

| Lipid | MW (mg/mmol) | Mg Lipid | μmol | Molar Ratio | Stock (mg/ml) | μl (1 ml) |
|---|---|---|---|---|---|---|
| DSPC | 790.16 | 5.0373 | 6.3751 | 2 | 25 | 201.49 |
| DOPE | 744.04 | 2.3716 | 3.1875 | 1 | 25 | 94.87 |
| PEG(2000)-DSPE | 2805.54 | 17.8855 | 6.3751 | 2 | 25 | 715.42 |
| PEG(750)-C8 | 1244.64 | 7.9347 | 6.3751 | 2 | 25 | 317.39 |
| Dihexadecyl Phosphate | 546.86 | 2.4138 | 4.4140 | 1 | 25 | 96.55 |
| C6-Cer | 397.64 | 3.3148 | 8.3361 | 3 | 25 | 132.59 |
| Total | x | 38.9577 | 35.0628 | 11 | 25 | 1558.31 |

Abbreviations for Table IV: DSPC, distearoylphosphatidylcholine; DOPE dioleoylphosphatidylethanolamine; PEG (2000) DSPE, polyethyleneglycol 2000 distearoylphosphatidylethanolamine; PEG(750) C8, N-Octanoyl-Sphingosine-1-succinyl(methoxy(polyethylene)glycol)750; C6-Cer, C6 ceramide.

Liposomes are made according to the procedure described in Example 1 using the materials and amounts listed in Table IV to produce ceramide anionic liposomes including one or more encapsulated hydrophilic antineoplastic chemotherapeutic drugs, such as sorafenib and cladribine, or other vinca alkyloids such as vincristine, vinglycinate, vinorelbine and vindesine, to obtain similar drug loading and anti-cancer effects.

Example 5

Normal and cancer cell viability in the presence or absence of a pharmaceutical composition can be determined according to a well-known MTS method.

MTS (3-(4,5-dimethylthiazol-2-yl)-5-(3-carboxymethoxyphenyl)-2-(4-sulfophenyl)-2H-tetrazolium), in the presence of phenazine methosulfate (PMS), produces a reduced formazan product, whose purple color can be assessed. In living cells, reduced formazan has an absorbance maximum at 490-500 nm in phosphate-buffered saline. The MTS assay is often described as a 'one-step' MTT assay, which offers the convenience of adding the reagent straight to the cell culture without the intermittent steps required in the MTT assay. However this convenience makes the MTS assay susceptible to cololmetric interference as the intermittent steps in the MTT assay remove traces of colored compounds, whilst these remain in the microtiter plate in the one-step MTS assay.

Figure 3A:
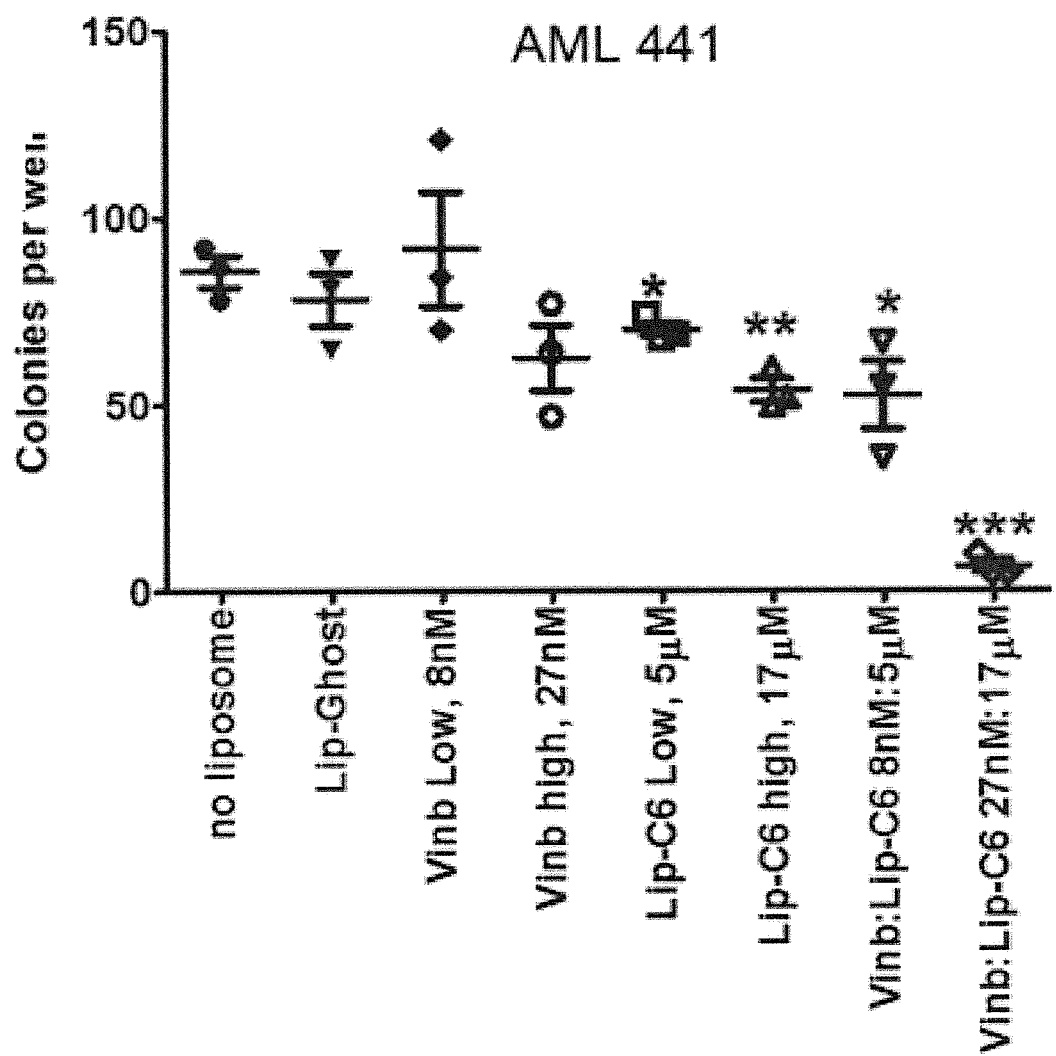
FIG. 3A is a graph showing that vinblastine potentiates the inhibitory activity of ceramide anionic liposome compositions of the present invention including vinblastine on growth and survival of primary human acute myeloid leukemia cells of poor prognosis in semisolid media for clonogeneic growth.

Vinblastine potentiates the inhibitory activity of C6 ceramide nanoliposomes upon growth and survival of cultured primary human AML of poor prognosis (#441) in semisolid media for clonogeneic growth as shown in FIG. 3A.

For FIG. 3A, primary human AML cells (n=5) were thawed and grown for 12-14 days in semi-solid medium with the indicated concentration of Lip-C6 or Lip-ghost and/or vinblastine. Ceramide inhibits colony formation in a dose-dependent manner.

Figure 3B:
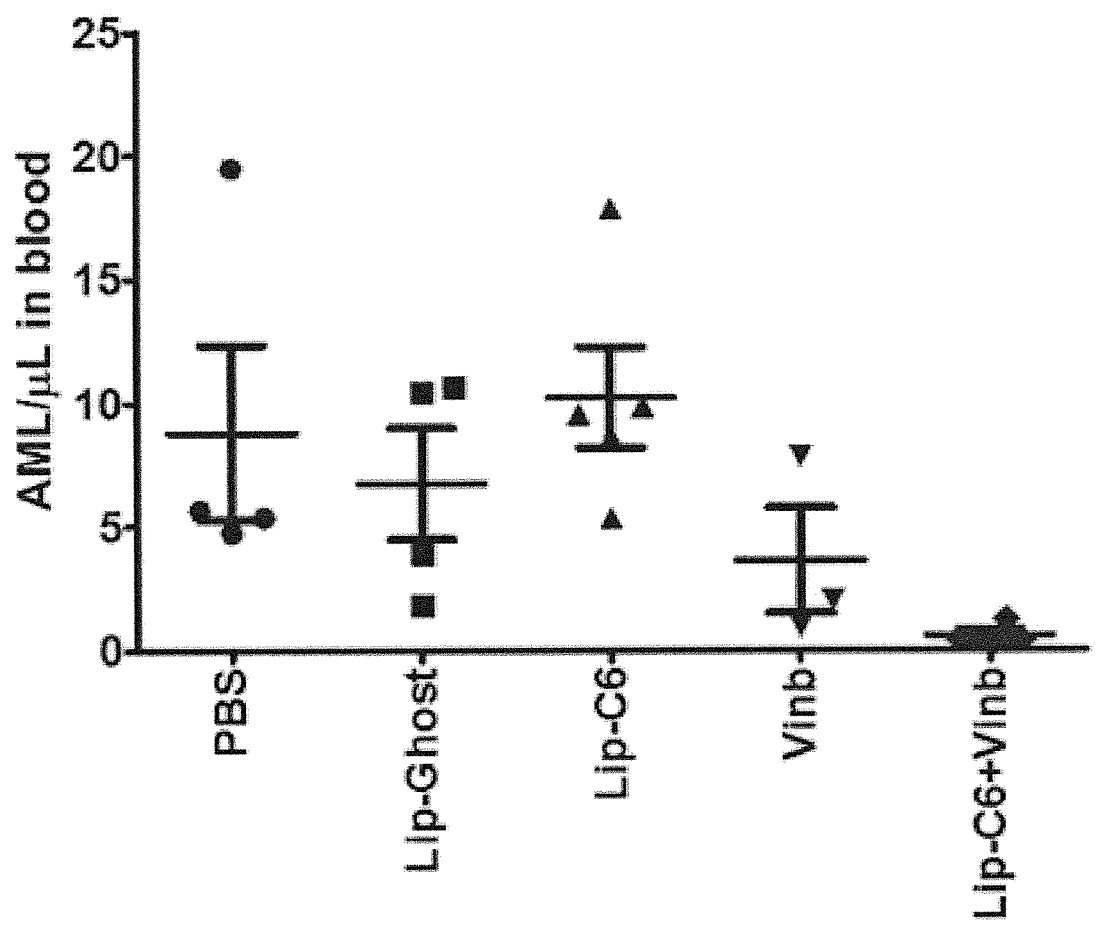
FIG. 3B is a graph showing in vivo activity of ceramide anionic liposome compositions of the present invention including vinblastine on blood burden of human acute myeloid leukemia cells in Nod Scid Gamma (NSG) mice.

In vivo therapeutic activity of C6-VBL ("combo") nanoliposomes prepared as described in Example 1 is tested against poor prognosis hAML #329 cells growing in NSG mice. FIG. 3B shows the blood burden of human AML (in 1000 cells/ul of blood) and the effect of compound C6-VBL ("combo") nanoliposomes prepared as described in Example 1 vs control PBS or ghost nanoliposomes (p-0.0007 and 0.0022 respectively).

Figure 3C:
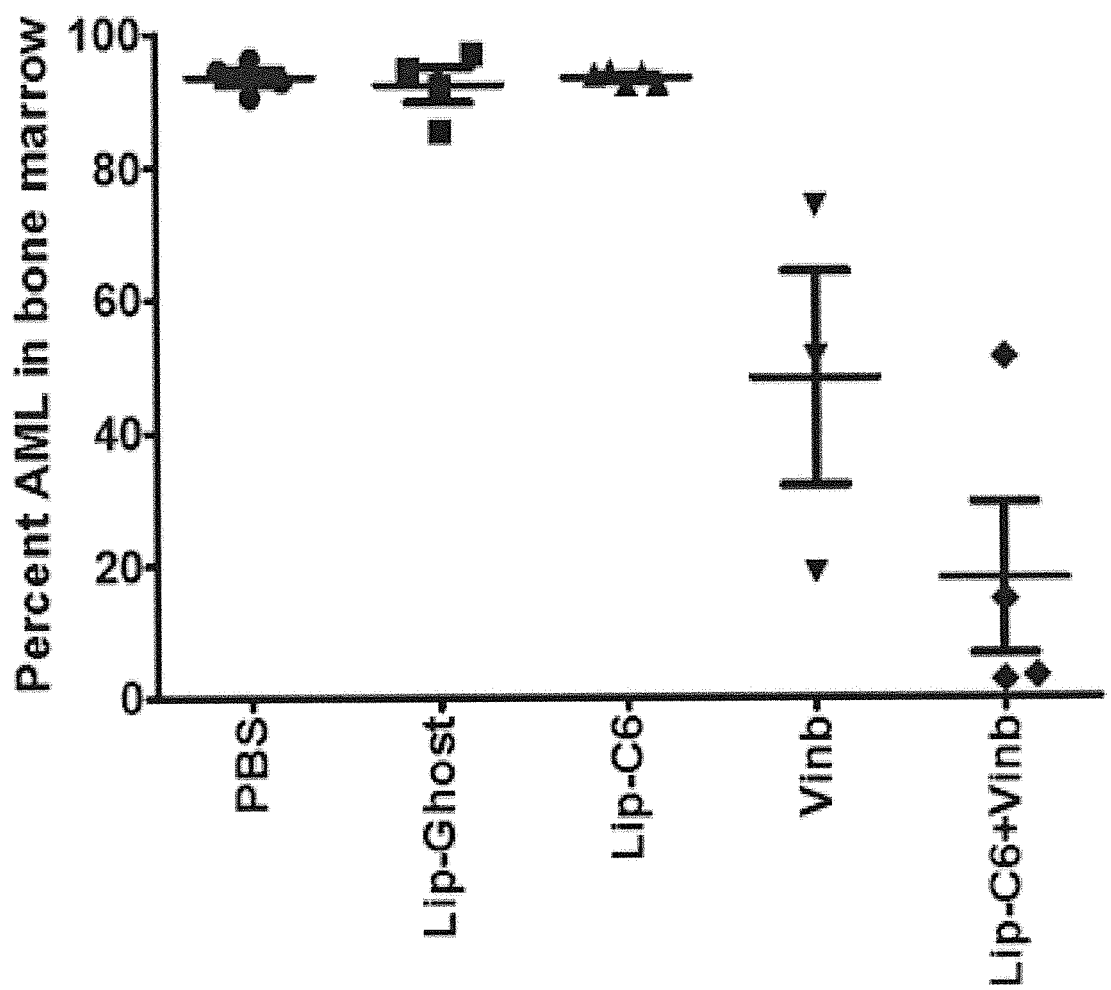
FIG. 3C is a graph showing in vivo activity of ceramide anionic liposome compositions of the present invention including vinblastine on bone marrow burden of human acute myeloid leukemia cells in Nod Scid Gamma (NSG) mice.

FIG. 3C shows similar results demonstrated for marrow replacement by hAML 329. C6, Ghost, and PBS are all significantly different than C6-VBL ("combo") nanoliposomes prepared as described in Example 1 (p=0.0009, 0.0016, and 0.0015 respectively). Similar results may be obtained using the ceramide anionic nanoliposomes of Examples 2-4 and 6-10.

Example 6

Table V shows amounts of the indicated materials included in liposomes used in this example.

TABLE V

| Lipid | MW (mg/mmol) | Mg Lipid | umol | Molar Ratio | Stock (mg/ml) | ul (1 ml) |
|---|---|---|---|---|---|---|
| DSPC | 790.16 | 9.4450 | 11.9532 | 3.75 | 25 | 377.80 |
| DOPE | 744.04 | 4.1504 | 5.5782 | 1.75 | 25 | 166.02 |
| PEG(2000)-DSPE | 2805.54 | 4.4714 | 1.5938 | 0.5 | 25 | 178.85 |
| PEG(750)-C8 | 1244.64 | 1.9837 | 1.5938 | 0.5 | 25 | 79.35 |
| Dihexadecyl Phosphate | 546.86 | 2.4138 | 4.4140 | 1 | 25 | 96.55 |
| C8-Cer | 425.7 | 3.5487 | 8.3361 | 3 | 25 | 141.95 |
| Total | x | 26.0129 | 33.4690 | 10.5 | 25 | 1040.52 |

Abbreviations for Table IV:DSPC, distearoylphosphatidylcholine; DOPE dioleoylphosphatidylethanolamine; PEG (2000) DSPE, polyethyleneglycol 2000 distearoylphosphatidylethanolamine; PEG(750) C8, N-Octanoyl-Sphingosine-1-succinyl(methoxy(polyethylene)glycol)750; C8-Cer, C8 ceramide.

Liposomes are made according to the procedure described in Example 1 using the materials and amounts listed in Table V to produce ceramide anionic liposomes including one or more encapsulated hydrophilic antineoplastic chemotherapeutic drugs, such as sorafenib and cladribine, or other vinca alkyloids such as vincristine, vinglycinate, vinorelbine and vindesine, to obtain similar drug loading and anti-cancer effects.

Example 7

In this example, the lipids listed in Table II are combined in a mixture, dried under nitrogen to remove solvents and then rehydrated in phosphate buffered saline, pH 7.4, at 65 degrees Celsius for up to 3 hours, followed by sonication for two minutes. Five milligrams vincristine in 100 microliters of phosphate buffered saline/0.9% NaCl is added to 900 microliters of the lipid mixture such that the drug concentration is 5 mg/mL and the drug:lipid ratio is 5 mg drug:27.59 mg lipid, followed by overnight incubation (12-18 firs) at room temperature. After the overnight incubation, the mixture is warmed to 65 degrees Celsius for 30 minutes, followed by a second sonication at 65 degrees Celsius for 5 minutes until translucent and then extrusion at 68 degrees Celsius using a 100 nM filter within a miniextruder (9 passages), to produce a "final product" of ceramide anionic liposomes encapsulating 3 to 4 mg of vincristine.

To demonstrate anti-cancer activity, DLD 1 human colon cancer cells are treated with ceramide anionic liposomes that contain 0.01 µM vincristine, 0.1 µM vincristine, 1 µM vincristine, PBS or varying amounts of the ceramide anionic liposomes of Example 1. Controls can be ghost liposomes containing no ceramide, vincristine or vinblastine; or unencapsulated (free) vinblastine or vincristine at similar concentrations.

Example 8

In this example, the lipids listed in Table V are combined in a mixture, dried under nitrogen to remove solvents and then rehydrated in phosphate buffered saline, pH 7.4, at 65 degrees Celsius for up to 3 hours, followed by sonication for two minutes. Five milligrams vinblastine in 100 microliters of phosphate buffered saline/0.9% NaCl is added to 900 microliters of the lipid mixture such that the drug concentration is 5 mg/mL and the drug:lipid ratio is 5 mg drug:26.01 mg lipid, followed by overnight incubation (12-18 hrs) at room temperature. After the overnight incubation, the mixture is warned to 65 degrees Celsius for 30 minutes, followed by a second sonication at 65 degrees Celsius for 5 minutes until translucent and then extrusion at 68 degrees Celsius using a 100 nM filter within a miniextruder (9 passages), to produce a "final product" of ceramide anionic liposomes encapsulating 3 to 4 mg of vinblastine.

To demonstrate anti-cancer activity, DLD1 human colon cancer cells are treated with ceramide anionic liposomes that contain 0.01 µM vinblastine, vinblastine, 1 µM vinblastine or PBS. Controls can be ghost liposomes containing no ceramide or vinblastine; or unencapsulated (free) vinblastine at similar concentrations.

Example 9

In this example, the lipids listed in Table II are combined in a mixture, dried under nitrogen to remove solvents and then rehydrated in phosphate buffered saline, pH 7.4, at 65 degrees Celsius for up to 3 hours, followed by sonication for two minutes. Five milligrams cladribine in 100 microliters of phosphate buffered saline/0.9% NaCl is added to 900 microliters of the lipid mixture such that the drug concentration is 5 mg/mL and the drug:lipid ratio is 5 mg drug:27.59 mg lipid, followed by overnight incubation (12-18 hrs) at room temperature. After the overnight incubation, the mixture is warmed to 65 degrees Celsius for 30 minutes, followed by a second sonication at 65 degrees Celsius for 5 minutes until translucent and then extrusion at 68 degrees Celsius using a 100 nM filter within a miniextruder (9 passages), to produce a "final product" of ceramide anionic liposomes encapsulating 3 to 4 mg of cladribine.

To demonstrate anti-cancer activity, MDA-MB-468 human breast cancer cells are treated with ceramide anionic liposomes that contain 0.01 µM cladribine, 0.1 µM cladribine, 1 µM cladribine, PBS or varying amounts of the ceramide anionic liposomes of Example 1. Controls can be ghost liposomes containing no ceramide, cladribine or vinblastine; or unencapsulated (free) vinblastine or cladribine at similar concentrations.

Example 10

In this example, the lipids listed in Table I are combined in a mixture, dried under nitrogen to remove solvents and then rehydrated in phosphate buffered saline, pH 7.4, at 65 degrees Celsius for up to 3 hours, followed by sonication for two minutes. Five milligrams sorafenib in 100 microliters of phosphate buffered saline/0.9% NaCl is added to 900 microliters of the lipid mixture such that the drug concentration is 5 mg/mL and the drug:lipid ratio is 5 mg drug:27.59 mg lipid, followed by overnight incubation (12-18 hrs) at room temperature. After the overnight incubation, the mixture is warmed to 65 degrees Celsius for 30 minutes, followed by a second sonication at 65 degrees Celsius for 5 minutes until translucent and then extrusion at 68 degrees Celsius using a 100 nM filter within a miniextruder (9 passages), to produce a "final product" of ceramide anionic liposomes encapsulating 3 to 4 mg of sorafenib.

To demonstrate anti-cancer activity, SK-HEP-1 human hepatocellular cancer cells and UACC-903 human melanoma cells are treated with ceramide anionic liposomes that contain 0.01 µM sorafenib, 0.1 µM sorafenib, 1 µM sorafenib, PBS or varying amounts of the ceramide anionic liposomes of Example 1. Controls can be ghost liposomes containing no ceramide, sorafenib or vinblastine; or unencapsulated (free) vinblastine or sorafenib at similar concentrations.

Any patents or publications mentioned in this specification are incorporated herein by reference to the same extent as if each individual publication is specifically and individually indicated to be incorporated by reference.

The compositions and methods described herein are presently representative of preferred aspects, exemplary, and not intended as limitations on the scope of the invention. Changes therein and other uses will occur to those skilled in the art. Such changes and other uses can be made without departing from the scope of the invention as set forth in the claims.

The invention claimed is:

1. A pharmaceutical composition, comprising:
a antineoplastic chemotherapeutic encapsulated in ceramide anionic liposomes, wherein the liposomes comprise at least one pegylated neutral lipid, wherein the total amount of pegylated neutral lipid is an amount in the range of 5-20 Molar percent, inclusive, and wherein at least half of the amount of the pegylated neutral lipid is N-Octanoyl-Sphingosine-1-succinyl(methoxy(polyethylene)glycol)750 (PEG(750) C8); at least one anionic lipid, wherein the total amount of anionic lipid is an amount in the range of 5-15 Molar percent, inclusive; one or more ceramides selected from C4 ceramide, C6 ceramide, C8 ceramide, C10 ceramide, C12 ceramide, C14 ceramide, C16 ceramide and C18 ceramide, in an amount in the range of 1-40 Molar percent, inclusive; and cationic or neutral lipids, with the proviso that the resulting ceramide anionic liposomes have a net negative charge at physiological pH.

2. The pharmaceutical composition of claim 1, wherein the antineoplastic chemotherapeutic is an antineoplastic vinca alkaloid.

3. The pharmaceutical composition of claim 2, wherein the antineoplastic chemotherapeutic is selected from the group consisting of: vinblastine, vincristine, vinglycinate, vinorelbine, vindesine, sorafenib, cladribine and a combination of any two or more thereof.

4. The pharmaceutical composition of claim 1, wherein the ceramide anionic liposomes comprise a 3-5.5:1-4:1:3 ratio of neutral lipid:pegylated neutral lipid:anionic lipid:C4-C18 ceramide.

5. The pharmaceutical composition of claim 4, wherein the neutral lipid is a mixture of DSPC and DOPE, wherein the pegylated neutral lipid is a mixture of PEG(2000)-DSPE and N-Octanoyl-Sphingosine-1-succinyl(methoxy(polyethylene)glycol)750, and wherein the anionic lipid is dihexadecyl phosphate.

6. The pharmaceutical composition of claim 1, wherein the antineoplastic chemotherapeutic is vinblastine.

7. A method of producing a pharmaceutical composition, comprising:
providing a lipid mixture comprising at least one pegylated neutral lipid, wherein the total amount of pegylated neutral lipid is an amount in the range of 5-20 Molar percent, inclusive, and wherein at least half of the amount of the pegylated neutral lipid is N-Octanoyl-Sphingosine-1-succinyl(methoxy(polyethylene)glycol)750 (PEG(750) C8); at least one anionic lipid, wherein the total amount of anionic lipid is an amount in the range of 5-15 Molar percent, inclusive; one or more ceramides selected from C4 ceramide, C6 ceramide, C8 ceramide, C10 ceramide, C12 ceramide, C14 ceramide, C16 ceramide and C18 ceramide, in an amount in the range of 1-40 Molar percent, inclusive; and cationic or neutral lipids, with the proviso that the resulting lipid mixture has a net negative charge at physiological pH;
sonicating the lipid mixture in the presence of an amount of a antineoplastic chemotherapeutic at a temperature in the range of 55-75 degrees Celsius, inclusive, to produce a sonicated mixture; and
passing the sonicated mixture through a filter having pores of a desired size to produce liposomes having the desired size, at a temperature in the range of 67-75 degrees Celsius, producing a population of ceramide anionic liposomes, wherein the population comprises greater than 10% of the amount of the antineoplastic chemotherapeutic.

8. The method of claim 7, wherein the population comprises greater than 25% of the amount of the antineoplastic chemotherapeutic.

9. The method of claim 7, wherein the population comprises 15-75% of the amount of the antineoplastic chemotherapeutic.

10. The method of claim 7, wherein the ceramide is C6 ceramide, C8 ceramide or a combination of C6 ceramide and C8 ceramide.

11. The method of claim 7, wherein the antineoplastic chemotherapeutic is a vinca alkyloid antineoplastic chemotherapeutic.

12. The method of claim 7, wherein the antineoplastic chemotherapeutic is selected from the group consisting of: vinblastine, vincristine, vinglycinate, vinorelbine, vindesine, sorafenib, cladribine and a combination of any two or more thereof.

13. The method of claim 7, wherein the antineoplastic chemotherapeutic is vinblastine.

* * * * *